US010258662B2

(12) United States Patent
Lee et al.

(10) Patent No.: US 10,258,662 B2
(45) Date of Patent: Apr. 16, 2019

(54) COMPOSITION FOR PREVENTING OR TREATING HEPATITIS C INCLUDING VITIDIS VINFERAE RADIX EXTRACT OR FRACTION THEREOF AS ACTIVE INGREDIENT

(71) Applicants: DONGGUK UNIVERSITY INDUSTRY-ACADEMIC COOPERATION FOUNDATION, Seoul (KR); CATHOLIC UNIVERSITY INDUSTRY ACADEMIC COOPERATION FOUNDATION, Seoul (KR)

(72) Inventors: Choongho Lee, Goyang-si (KR); Tae Hwe Heo, Bucheon-si (KR); Kee Dong Yoon, Bucheon-si (KR)

(73) Assignees: DONGGUK UNIVERSITY INDUSTRY-ACADEMIC COOPERATION FOUNDATION, Seoul (KR); CATHOLIC UNIVERSITY INDUSTRY ACADEMIC COOPERATION FOUNDATION, Seoul (KR)

(*) Notice: Subject to any disclaimer, the term of this patent is extended or adjusted under 35 U.S.C. 154(b) by 488 days.

(21) Appl. No.: 14/894,210

(22) PCT Filed: Apr. 29, 2014

(86) PCT No.: PCT/KR2014/003793
§ 371 (c)(1),
(2) Date: Nov. 25, 2015

(87) PCT Pub. No.: WO2014/193088
PCT Pub. Date: Dec. 4, 2014

(65) Prior Publication Data
US 2016/0101143 A1 Apr. 14, 2016

(30) Foreign Application Priority Data

May 31, 2013 (KR) .................. 10-2013-0062609
Dec. 4, 2013 (KR) .................. 10-2013-0149928

(51) Int. Cl.
*A61K 36/87* (2006.01)

(52) U.S. Cl.
CPC .......... *A61K 36/87* (2013.01); *A61K 2236/33* (2013.01); *A61K 2236/331* (2013.01); *A61K 2236/333* (2013.01)

(58) Field of Classification Search
CPC .................................. A61K 36/87

USPC ......................................... 424/766
See application file for complete search history.

(56) References Cited

U.S. PATENT DOCUMENTS

| 4,927,817 A * | 5/1990 | Inagaki | A61K 38/04 514/184 |
| 2003/0216340 A1* | 11/2003 | Van Nest | A61K 31/7088 514/44 R |
| 2004/0171689 A1* | 9/2004 | Desreumaux | C12Q 1/6897 514/559 |
| 2005/0107277 A1* | 5/2005 | Lin | C08G 65/329 510/320 |
| 2006/0105063 A1* | 5/2006 | Hann | A61K 31/7004 424/744 |
| 2013/0029948 A1* | 1/2013 | Roppe | C07D 403/04 514/171 |

FOREIGN PATENT DOCUMENTS

| JP | 2010-155840 A | 7/2010 |
| KR | 10-2009-0103239 A | 10/2009 |
| KR | 10-2012-0081365 A | 7/2012 |
| KR | 10-1162710 B1 | 7/2012 |
| KR | 10-1221623 B1 | 1/2013 |
| KR | 10-2013-0022737 A | 3/2013 |

OTHER PUBLICATIONS

Sharma et al. Acta Poloniae Pharmaceutica—Drug Research. 2012. vol. 69, No. 5, pp. 933-937.*
Kim et al. J. Nutr. Sci. Vitaminol. 2012. vol. 58, pp. 187-194.*
Deng et al. J. Ethnopharmacol. 2012. Vo.. 142, pp. 795-803.*
Cheung et al. World J. Gastroenterol. 2006. vol. 12, No. 12, pp. 1912-1917.*
Liu et al., "Evaluation on Anti-hepatitis Viral Activity of Vitis vinifer L", Molecules, vol. 15, No. 10, pp. 7415-7422, (2010).
Orhan et al., "Hepatoprotective effect of Vitis vinifera L. leaves on carbon tetrachloride-induced acute liver damage in rats", Journal of Ethnopharmacology, vol. 112, No. 1, pp. 145-151, (2007).

* cited by examiner

*Primary Examiner* — Christopher R Tate
(74) *Attorney, Agent, or Firm* — Vorys, Sater, Seymour & Pease LLP; Mih Suhn Koh

(57) ABSTRACT

Provided is a method for preventing or treating hepatitis C by administrating a composition including, as an active ingredient, a Vitidis Vinferae Radix extract or a fraction thereof and, more specifically, to a Vitidis Vinferae Radix extract which is extracted with water and alcohol or a mixed solvent thereof, or a fraction thereof, which have remarkably low hepatotoxicity and exhibit an excellent effect of selectively inhibiting genome replication of a hepatitis C virus, and thus can be useful for preventing or treating hepatitis C.

3 Claims, 5 Drawing Sheets

COMPOSITION FOR PREVENTING OR TREATING HEPATITIS C INCLUDING VITIDIS VINFERAE RADIX EXTRACT OR FRACTION THEREOF AS ACTIVE INGREDIENT

TECHNICAL FIELD

The present invention relates to a composition for preventing or treating hepatitis C including a Vitidis Vinferae Radix extract or a fraction thereof as an active ingredient.

BACKGROUND ART

Collectively, liver cancer and liver disease are included as one of the four diseases recording the highest deaths per 100,000 people in addition to cerebrovascular disease, heart disease and respiratory disease. Viral hepatitis resulting from hepatitis B and C viruses accounts for 83% of total cases of the liver cancer and liver disease. Among them, the hepatitis C virus is a medically important pathogen accounting for about 170 million infected people around the world. The hepatitis C virus had been classified as a non-A non-B post-transfusion associated hepatitis (NANB) until the mid-1980s, and had been determined to be a disease caused by infection by an entirely new virus in 1989. After that, various researches and developments on the hepatitis C virus have been carried out.

Most cases of infection of liver cells due to the hepatitis C virus developed chronic hepatitis, and specifically, developed chronic liver diseases such as cirrhosis and liver cancer over a long period of 15 to 20 years, and thus is fatal. Further, it has been reported that 8,000 to 10,000 people per year have died of chronic hepatitis, cirrhosis and liver cancer due to the hepatitis C virus (HCV) in the U.S. Especially, most patients with end-stage hepatitis C died because they had waited for a liver transplant, but could not receive a liver transplant. Statistically, it is known that about 1.5% of the population is infected by the hepatitis C virus in Korea.

The hepatitis C virus (HCV) is the only virus classified as a hepacivirus in the Flaviviridae group, and has a single-stranded RNA consisting of approximately 9,600 nucleotides as a virus genome. The RNA is translated into a single polyprotein of about 3,000 amino acids, and the translated polyprotein is expressed as 10 types of different virus proteins by a signal peptidase in the endoplasmic reticulum of a hepatocyte and a NS3 protease which is one of the non-structural viral proteins. In the expressed virus proteins, structural proteins such as E1 and E2 which are envelope glycoproteins and the core which is a capsid protein are used to produce virus particles, and non-structural proteins such as NS2, NS3, NS4A, NS4B, NS5A and NS5B are used to produce a virus genome replication complex for replicating virus genomes. The HCV produces a virus genome replication complex from a membrane generated in the endoplasmic reticulum to replicate a RNA genome of a virus. A virus genome replication complex is enveloped by a membrane and remains invaginated to form an independent structure isolated from an external environment, and non-structural proteins are expressed in this structure, the expressed non-structural proteins serve as a replication factory of virus genomes in addition to NS5B proteins which are RNA polymerases of viruses. However, it has been unknown how this virus genome replication complex is produced and maintained. Especially, NS4B proteins in non-structural proteins of viruses have been determined to play a decisive role in forming a membranous web having a multi-vesicular structure which is necessary for genome replication of viruses in liver cells. The membranous web structure formed by the NS4B proteins is believed to provide a physical structure which is indispensable to produce a virus genome replication complex. Furthermore, NS5A proteins are known to play an important role in forming actual virus particles by assembling a virus genome replication complex using non-structural viral proteins of different viruses and transferring the thus formed virus genome to a lipid droplet structure to combine the virus genome with core proteins of viruses. Especially, a protein-protein interaction between the non-structural proteins of viruses is known to play a decisive role in producing a virus genome replication complex, but it is not yet well known what role it exactly plays on the molecular level.

Types of antivirals which can remedy viral diseases include indirect-acting antivirals (IAAs) which indirectly attack viruses according to a mechanism of antiviral action and direct-acting antivirals (DAAs) which directly attack viruses. Interferon alpha secreted in vivo when pathogenic microorganisms such as viruses penetrate the body is representative of antiviral innate immunity-boosting substances. Since interferon alpha increases an antiviral immune response of the host cells with the virus to block the cellular proliferation of viruses rather than attack viruses themselves, interferon alpha is effective for various types of viral diseases, and there is low probability of generation of mutant viruses having tolerance and resistance, because interferon alpha exhibits antiviral activity by adjusting the function of proteins of the host cells with viruses. However, antiviral specificity exhibiting antiviral activity only on specific viruses is significantly low. Accordingly, in order to overcome this problem, an amount of interferon more than an amount of interferon naturally secreted in vivo is used for therapeutic purposes, and thus serious side effects such as suicidal thoughts, depression and anemia and toxicity are caused.

Meanwhile, direct-acting antivirals which directly attack viruses selectively inhibit a specific function of virus proteins which is necessary for a life cycle of viruses unlike interferon, thus exhibiting high antiviral activity even at a relatively low concentration. Moreover, direct-acting antivirals have low toxicity and high safety as compared to indirect-acting antivirals. A reverse transcriptase inhibitor and protease inhibitor of the human immunodeficiency virus (HIV) are representative direct-acting antivirals, and respectively inhibit reverse transcriptases and proteases which are necessary for a life cycle of viruses, thus suppressing the cellular proliferation of viruses. However, there is relatively high probability of exhibiting resistance and tolerance to existing antivirals because a mutated virus changes the amino acid sequence of viral proteins targeted by antivirals. Especially, since RNA polymerases of the hepatitis C virus has no 5'-3' endonuclease activity serving to correct incorrect nucleic acids introduced during RNA genome replication, mutant viruses are easily formed while RNA which is a hepatitis C virus genome is replicated, and thus resistance and tolerance to direct-acting antivirals are easily formed.

An interferon-alpha and ribavirin currently used as a general hepatitis C therapeutic agent are indirect-acting antivirals (IAAs) which indirectly attack viruses by immune enhancement and inhibition of nucleic acid biosynthesis, respectively. However, even though two drugs described above are used together, a sustained virologic response (SVR) is less than 50% according to the genotype of viruses, and thus efficacy is very low. Further, serious side effects such as suicidal thoughts, depression and anemia and toxicity are also caused, and thus many hepatitis C patients abandon this treatment. Accordingly, there is a great need for the development of effective and safe drugs which can substitute for existing antiviral drugs for the hepatitis C virus.

Further, Vitidis Vinferae Radix is an herbal medicine which is the fresh root of *Vitis vinifera* or *Vitis amurensis* belonging to Vitaceae, or the root of *Vitis vinifera* or *Vitis amurensis* dried in the sun. Vitidis Vinferae Radix is the herbal medicine name of these roots. As for Vitidis Vinferae Radix, it is described that "water obtained by decocting Vitidis Vinferae Radix has an effect of stopping nausea and hiccups. Further, when a pregnant woman feels that her solar plexus is uncomfortable due to symptoms of pregnancy, the water works on this" in Dongui Bogam. Vitidis Vinferae Radix has an effect of expelling wind-damp and promoting urination, and thus has been used for remedy of brachialgia caused by rheumatism, phleboedesis, urine discomfort or the like from old times.

As described above, various pharmacological effects of Vitidis Vinferae Radix have been known, but effects of preventing, improving or treating hepatitis C have not been reported, and research in this area has also not been made.

The present inventors have continuously carried out research to develop novel hepatitis C therapeutic agents, and as a result, have found that a Vitidis Vinferae Radix extract or a fraction thereof has remarkably low hepatotoxicity and exhibits an excellent effect of selectively inhibiting genome replication of the hepatitis C virus, thus completing the present invention.

DISCLOSURE

Technical Problem

An objective of the present invention is to provide to a pharmaceutical composition for preventing or treating hepatitis C including a Vitidis Vinferae Radix extract or a fraction thereof as an active ingredient.

Another objective of the present invention is to provide to a food composition for preventing or improving hepatitis C including a Vitidis Vinferae Radix extract or a fraction thereof as an active ingredient.

However, the scope of the present invention is not limited to the above-described objects, and other unmentioned objects may be clearly understood by those skilled in the art from the following descriptions.

Technical Solution

In order to achieve the objectives of the invention, the present invention provides a pharmaceutical composition for preventing or treating hepatitis C or a food composition for preventing or improving hepatitis C, which includes a Vitidis Vinferae Radix extract or a fraction thereof as an active ingredient.

As an embodiment of the present invention, the Vitidis Vinferae Radix extract is prepared by extracting Vitidis Vinferae Radix using water, an alcohol having 1 to 4 carbon atoms or a mixed solvent thereof.

As the embodiment of the present invention, the alcohol having 1 to 4 carbon atoms includes methanol or ethanol.

As the embodiment of the present invention, the fraction includes an ethyl acetate fraction, a butanol fraction, a hexane fraction or a water fraction prepared by sequentially fractionating Vitidis Vinferae Radix using ethyl acetate, butanol, hexane and water.

As the embodiment of the present invention, the Vitidis Vinferae Radix extract or fraction thereof has a selective inhibitory activity on RNA genome replication of the hepatitis C virus.

Advantageous Effects

The Vitidis Vinferae Radix extract or fraction thereof according to the present invention has remarkably low hepatotoxicity and exhibits an excellent effect of selectively inhibiting genome replication of the hepatitis C virus, and thus can be useful for preventing or treating hepatitis C.

MODES OF THE INVENTION

Figure 1:
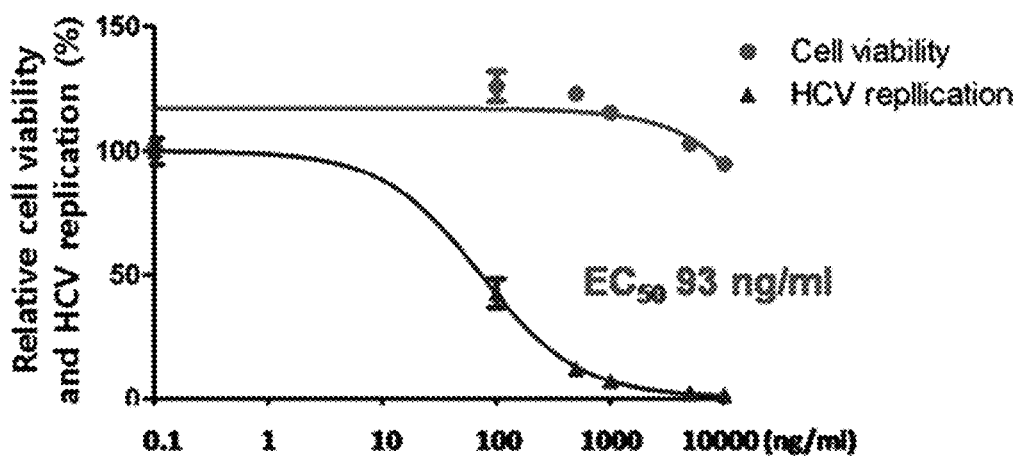
FIG. 1 is a view showing an influence of a methanol extract of Vitidis Vinferae Radix according to the present invention on genome replication and cell viability of the hepatitis C virus (●: cell viability, ▲Δ: HCV genome replication rate).

The present invention provides a composition for preventing or treating hepatitis C, including a Vitidis Vinferae Radix extract or a fraction thereof as an active ingredient.

The composition includes a pharmaceutical composition or a food composition.

Hereinafter, the present invention will be described in detail.

The Vitidis Vinferae Radix extract which is an active ingredient in the composition according to the present invention may be obtained by the following method.

First, Vitidis Vinferae Radix is cleaned with water, dried and ground. The Vitidis Vinferae Radix is not limited, and any Vitidis Vinferae Radix which is grown, commercially available or the like may be used without limitation. A solvent of which the weight is 1 to 10 times, preferably, 2 to 5 times the weight of the Vitidis Vinferae Radix is added into the ground Vitidis Vinferae Radix such that the Vitidis Vinferae Radix is fully immersed, and then extraction is performed for 1 to 5 hours, preferably, for about 2 hours. The extraction solvent may be at least one type of the solvent selected from water, an alcohol having 1 to 4 carbon atoms and a mixed solvent thereof without being limited thereto, and preferably, may be methanol or ethanol. An extraction method may include ultrasound extraction, subcritical extraction, high-temperature extraction, high-pressure extraction, filtration, reflux extraction or the like, and may include a conventional extraction method in the related field, preferably, may be ultrasound extraction, but is not limited thereto. Thereafter, the Vitidis Vinferae Radix extract is separated by centrifugation, the supernatant is collected and filtered, and the filtrate is condensed under reduced pressure and freeze-dried, thus preparing the Vitidis Vinferae Radix extract in a powder form. Further, after the Vitidis Vinferae Radix extract is suspended in distilled water, the Vitidis Vinferae Radix extract is sequentially fractionated using ethyl acetate, butanol and hexane, and thereby, a distilled water soluble residue is obtained.

The Vitidis Vinferae Radix extract according to the present invention has remarkably low hepatotoxicity and exhibits an excellent effect of selectively inhibiting genome replication of the hepatitis C virus, and thus may be useful for preventing or treating hepatitis C.

The composition according to the present invention may further include one or more types of well-known active ingredient having an effect of preventing or treating hepatitis C in addition to the Vitidis Vinferae Radix extract or a fraction thereof.

The composition according to the present invention may further include suitable carriers, excipients and diluents conventionally used in the preparation of pharmaceutical compositions. Moreover, the composition according to the present invention may be prepared into an oral formulation such as a powder formulation, a granule formulation, a tablet formulation, a capsule formulation, a suspension formulation, an emulsion formulation, a syrup formulation, an aerosol formulation or the like, and may be prepared into an external formulation, a suppository formulation, and a sterilized injection solution formation according to conventional methods.

Examples of carriers, excipient, or diluents that are available for use in the composition according to the present invention are lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, mineral oils, etc. When the composition is prepared into various formulations, a conventional diluent or excipient, such as a filler, a bulking agent, a binding agent, a wetting agent, an disintegrating agent, a surfactant or the like may be used.

A solid formulation for oral administration includes a tablet formulation, a pill formulation, a powder formulation, a granule formulation, a capsule formulation or the like, and these solid formulations are prepared by mixing one or more excipients, for example, starch, calcium carbonate, sucrose, lactose, or gelatin with the composition. Further, a lubricating agent such as magnesium stearate or talc may be used in addition to a simple excipient. A liquid formulation for oral administration may be a suspension formulation, an internal solution formulation, an oil formulation, a syrup formulation, etc. The liquid formulation may include various excipients, for example, a wetting agent, a sweetening agent, an aromatic, a preservative or the like in addition to a conventional simple diluent such as water or liquid paraffin. A formulation for non-oral administration includes a sterilized aqueous solution formulation, a non-aqueous solution formulation, a suspension formulation, an oil formulation, a lyophilized formulation, or a suppository formulation. Furthermore, propyleneglycol, polyethylene glycol, vegetable oils such as olive oil, and an injectable ester such as ethylolate may be used as the non-aqueous solution formulation and the suspension formulation. A substrate for the suppository formulation includes Witepsol, Macrogol, Tween 61, cacao butter, laurin butter, glycerogelatins, etc.

As used herein, the term "administration" denotes introducing a predetermined composition according to the present invention into an individual by any suitable method.

The preferable administration amount of the pharmaceutical composition according to the present invention may vary depending on the physical state and body weight of an individual, severity of illness, drug type, route and duration of administration, but may be suitably determined by those skilled in the art. 0.1 to 1,000 mg/kg, preferably, 0.001 to 200 mg/kg of the Vitidis Vinferae Radix extract or fraction thereof according to the present invention may be administered per day for the desired effect, and may be administered once a day or divided into several times of administration in a day.

The pharmaceutical composition according to the present invention may be administered via various routes. All of the administration methods are predictable, and for example, the composition may be administered orally or rectally, or by intravenous, muscular, subcutaneous, intrauterine subdural, or intracerebroventricular injection.

The composition according to the present invention may be used alone or in combination with methods including operating, radiation treatment, hormone treatment, chemical treatment and biological reaction regulation for preventing or treating hepatitis C.

As used herein, the term "health functional food" refers to a food having a body modulating function such as prevention of and recovery from diseases, body defense, recovery from illness, suppression of aging, etc. This health functional food is required to be harmless to the body when ingested for a long time. The Vitidis Vinferae Radix extract according to the present invention may be added into the health functional food for the purpose of preventing or treating hepatitis C. When the Vitidis Vinferae Radix extract according to the present invention is used as a food additive, the Vitidis Vinferae Radix extract itself may be added or may be used with other foods or food components, and may be suitably used according to conventional methods. An amount of an active ingredient to be mixed may be suitably determined according to the purpose thereof (for prevention, health, or therapeutic treatment). In general, the Vitidis Vinferae Radix extract according to the present invention may be added at 15 wt % or less, preferably, 10 wt % or less based on a raw material in the food or beverage production. However, when ingested for a long time for the purpose of health and hygiene or health control, the amount of the Vitidis Vinferae Radix extract may be below the above-described range. Further, since there is no problem in safety, the active ingredient may be used at an amount above the above-described range.

The type of the food is not particularly limited. Examples of foods to which the composition according to the present invention may be added include meats, sausages, bread, chocolate, candies, snack, confectionery, pizza, noodles, gum, dairy products including ice cream, various soups, beverages, teas, drinks, alcoholic beverages, multivitamin preparations, or the like, and include all of typical health foods.

The health beverage composition according to the present invention may additionally include various sweetening agents, natural carbohydrates or the like as in conventional beverages. The natural carbohydrates include monosaccharides such as glucose and fructose, disaccharides such as maltose and sucrose, and natural sweeteners such as dextrin and cyclodextrin, synthetic sweeteners such as saccharin and aspartame, etc. The content of the natural carbohydrates in the composition according to the present invention is generally in the range of about 0.01 to 10 g, preferably, about 0.01 to 0.1 g based on 100 ml of the composition.

In addition, the composition according to the present invention may include various nutrients, vitamins, electrolytes, flavoring agents, colorants, pectic acid or its salt, alginic acid or its salt, organic acids, protective colloidal thickeners, pH adjusters, stabilizers, preservatives, glycerin, alcohols, carbonating agents used in carbonated drinks, etc. Moreover, the composition according the present invention may include fruit flesh for the preparation of natural fruit juices, fruit juice beverages and vegetable juices. The above components may be used alone or by mixture. The content of these additives is not significantly critical, but is generally in the range of about 0.01 to 0.1 parts by weight based on 100 parts by weight of the composition according to the present invention.

Hereinafter, the present invention will be described in detail in accordance with preferred examples, experimental examples and preparation examples. However, the following examples, experimental examples and preparation examples are provided for illustrative purposes only, and the scope of the present invention should not be limited thereto in any manner.

EXAMPLES

Example 1. Preparation of Vitidis Vinferae Radix Water Extract

Vitidis Vinferae Radix (purchased from the Kyung-Dong market, Deokhyeon-dang) was thoroughly cleaned with water, dried and ground. 500 ml of water was added to 100 g of the ground Vitidis Vinferae Radix, the Vitidis Vinferae Radix was immersed for 2 hours and was extracted by sonication extraction. Thereafter, the Vitidis Vinferae Radix extract was separated by centrifugation, the supernatant was collected and filtered, and the filtrate was condensed under reduced pressure and freeze-dried, thus preparing 14.1 g of the Vitidis Vinferae Radix extract in a powder form.

Example 2. Preparation of Vitidis Vinferae Radix Methanol Extract 9.1 g of a Vitidis Vinferae Radix methanol extract was obtained in the same manner as in Example 1 except that 100%-methanol was substituted for water in Example 1.

Example 3. Preparation of Fraction of Vitidis Vinferae Radix 8.3 g of a Vitidis Vinferae Radix ethanol extract was obtained in the same manner as in Example 1 except that ethanol was substituted for water in Example 1. The thus obtained Vitidis Vinferae Radix ethanol extract was suspended in distilled water, and sequentially fractionated using hexane, ethyl acetate, butanol and water, thereby preparing 0.7 g of a hexane fraction, 2.5 g of an ethyl acetate fraction, 2.1 g of a butanol fraction and 3 g of a water fraction.

Experimental Example 1. Analysis of Hepatotoxicity of Vitidis Vinferae Radix Extract The following experiment was performed using an EZ-Cytox cell viability assay (Daeil Lab Service) which is a conventional method, in order to determine hepatotoxicity of the Vitidis Vinferae Radix methanol extract obtained in Example 2.

First, Huh 7.5 human liver cancer cells were added to a 96 well-plate at $1.7\times10^4$ to $2.0\times10^4$ cells/well, and incubated in an incubator at 37° C. for 24 hours. The cells were treated with the Vitidis Vinferae Radix methanol extracts having various concentrations in the range of 0.1 ng/ml to 10 μg/ml, and incubated for 72 hours. A control group was treated with dimethyl sulfoxide (DMSO). Thereafter, a culture fluid was discarded, the cells were cleaned with PBS, added with 100 μl of a $\frac{1}{10}$ (v/v) diluted solution prepared by adding a cell culture fluid to an EZ-Cytox reagent including water-soluble tetrazolium salts, and reacted for 3 hours. After the reaction, the absorbance of the cells was measured by a spectrophotometer using light with a wavelength of 450 nm. A relative absorbance of the cells when treated with the Vitidis Vinferae Radix methanol extract was calculated based on an absorbance of 100 when treated with DMSO, and results were shown in FIG. 1.

As a result, as shown in FIG. 1, it was determined that the cells treated with the Vitidis Vinferae Radix methanol extract at a concentration of 0.1 ng/ml to 10 μg/ml exhibited excellent cell viability, and had significantly low hepatotoxicity, thus ensuring high safety.

Experimental Example 2. Measurement of Inhibitory Activity on RNA Genome Replication of Hepatitis C Virus of Vitidis Vinferae Radix Extract or Fraction Thereof The following experiment was performed in order to measure selective inhibitory activity on RNA genome replication of the hepatitis C virus of the Vitidis Vinferae Radix methanol extract obtained in Example 2 or the Vitidis Vinferae Radix ethanol extract obtained in Example 3 and fractions thereof.

2-1. Preparation of Reporter Virus for Measuring Genome Replication of Hepatitis C Virus An FL-J6/JFH-5C19Rluc2AUbi HCV replicon of genotype 2a was used as a reporter virus for measuring genome replication of the hepatitis C virus. The genome structure diagram of the reporter virus was shown in FIG. 2.

Figure 2:
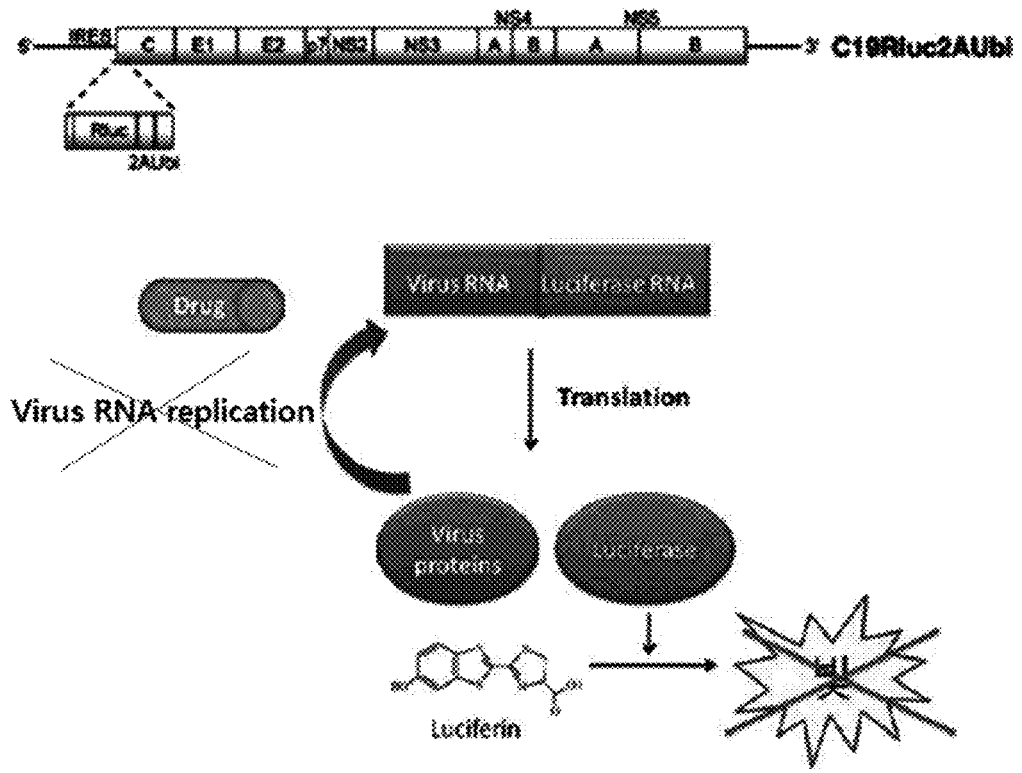
FIG. 2 is a view showing a genome structure of an HCV replicon FL-J6/JFH-5C19Rluc2AUbi HCV reporter virus used to measure genome replication of the hepatitis C virus, and a principle of finding a virus genome replication inhibitor.
Figure 3:
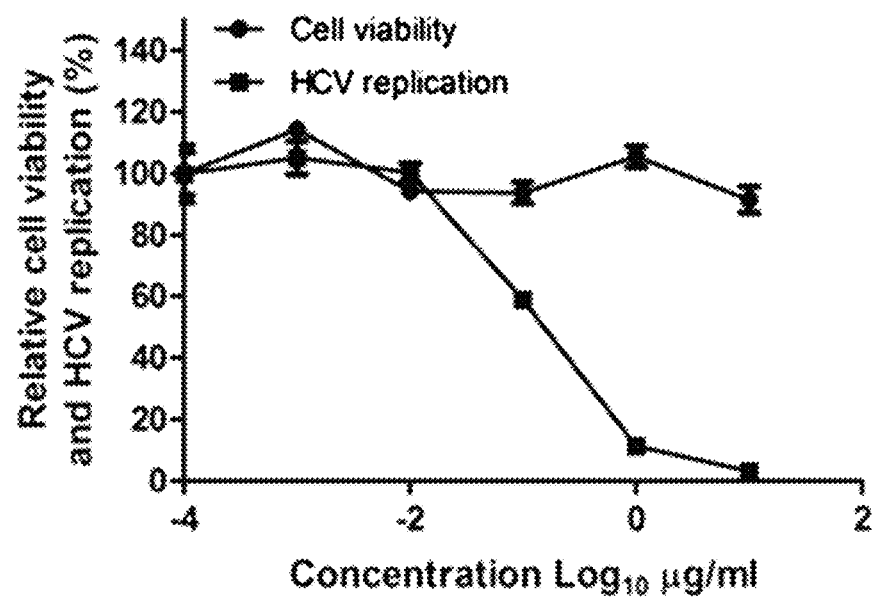
FIG. 3 is a view showing an influence of an ethyl acetate fraction of Vitidis Vinferae Radix according to the present invention on genome replication and cell viability of the hepatitis C virus (●: cell viability, Δ: HCV genome replication rate).
Figure 4:
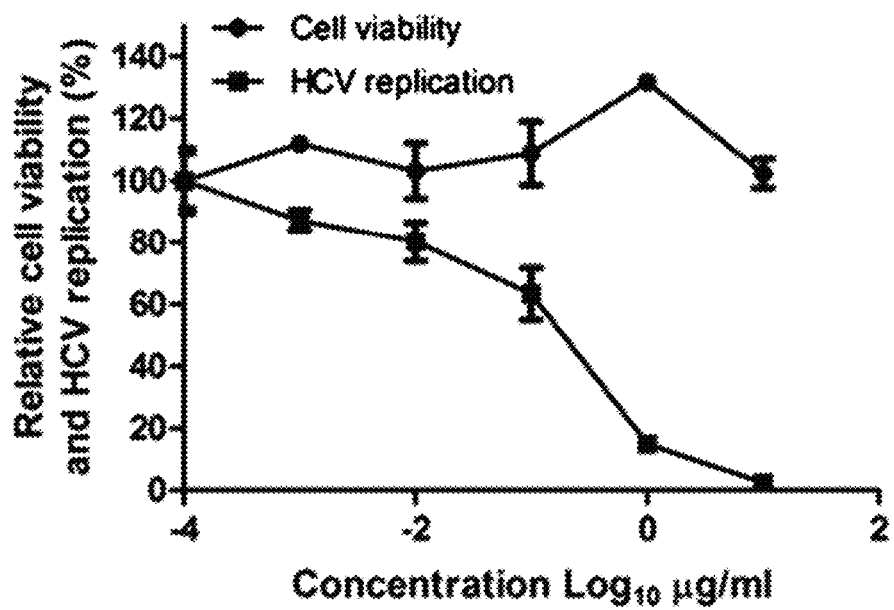
FIG. 4 is a view showing an influence of a butanol fraction of Vitidis Vinferae Radix according to the present invention on genome replication and cell viability of the hepatitis C virus (●: cell viability, Δ: HCV genome replication rate).
Figure 5:
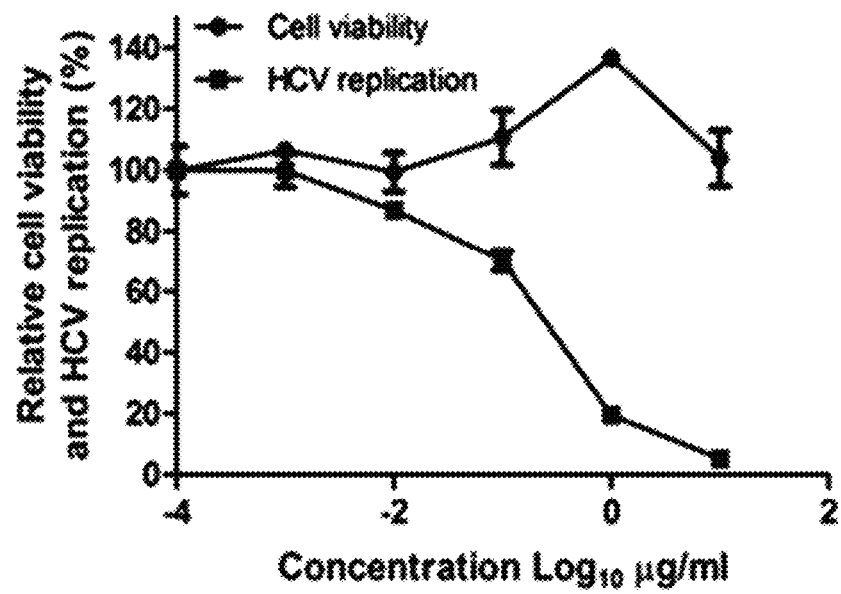
FIG. 5 is a view showing an influence of an ethanol extract of Vitidis Vinferae Radix according to the present invention on genome replication and cell viability of the hepatitis C virus (●: cell viability, Δ: HCV genome replication rate).
Figure 6:
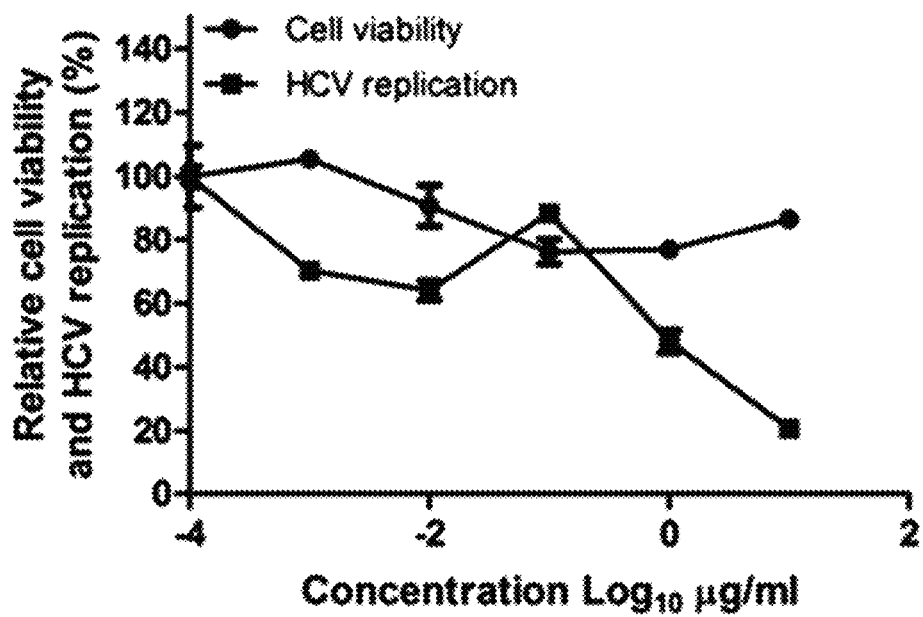
FIG. 6 is a view showing an influence of a hexane fraction of Vitidis Vinferae Radix according to the present invention on genome replication and cell viability of the hepatitis C virus (●: cell viability, Δ: HCV genome replication rate).
Figure 7:
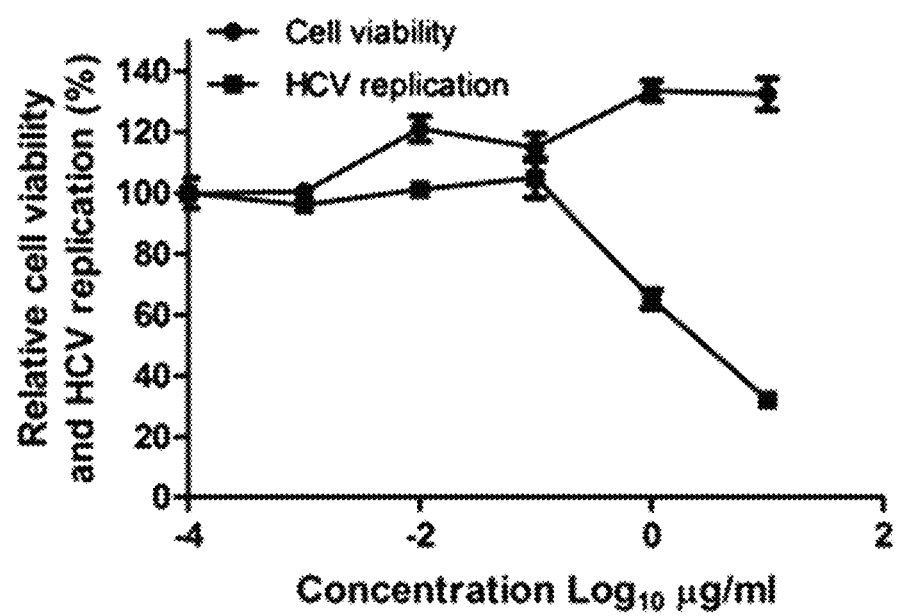
FIG. 7 is a view showing an influence of a water extract of Vitidis Vinferae Radix according to the present invention on genome replication and cell viability of the hepatitis C virus (●: cell viability, Δ: HCV genome replication rate).

As shown in FIG. 2, the reporter virus includes cDNA of the entire genome of the hepatitis C virus of genotype 2a, and has Renilla luciferase and the Ubi sequence of a self-cleaving foot-and-mouth disease virus 2A protein attached between an internal ribosome entry site (IRES) of the virus and the core protein of the virus, and thus when HCV RNA obtained by in-vitro transcription of the FL-J6/JFH-5C19Rluc2AUbi plasmid using a T7 RNA polymerase is injected into Huh 7.5 cells which are hepatoma cell lines, RNA of the injected virus produces a polyprotein through translation using IRES. Here, Renilla luciferase in the produced polyprotein is isolated form a viral non-structural protein by means of the UBI sequence of the self-cleaving foot-and-mouth disease virus 2A protein, and RNA genome replication of the virus in liver cells may be indirectly measured by measuring the activity of the isolated Renilla luciferase.

2-2. Measurement of Inhibitory Activity on Genome Replication of Hepatitis C Virus of Vitidis Vinferae Radix Extract or Fraction Thereof Huh 7.5 human liver cells were trypsinized and resuspended using a PBS solution to have a cell density of $1.5 \times 10^7$ cells/ml. A total of 5 µg of FLJ6/JFH-5 C19Rluc2AUbi RNA transferred in vitro was mixed with 400 µl of a PBS buffer solution including Huh 7.5 human liver cells, and put into a 2-mm-gap cuvette (BTX). Here, 5 pulses were applied using a BTX 830 electroporator at 0.82 kV for 99 ms, and thereby Huh 7.5 human liver cells were transfected with the FL-J6/JFH-5 C19Rluc2AUbi RNA. The cells were treated with the Vitidis Vinferae Radix extracts or fractions thereof having various concentrations in the range of 0.1 ng/ml to 10 µg/ml, and incubated for 72 hours, 6 hours after the electroporation. A control group was treated with DMSO. Culture fluids of the cells treated with the materials were discarded, wells to which the cells were attached were cleaned with PBS, added with 20 µl, of a cell lysis buffer solution, and maintained in an ice bath for 20 minutes.

Thereafter, a Renilla luciferase matrix was diluted 100 times with a Renilla luciferase buffer solution to prepare a diluted solution, and 100 µl of the diluted solution was put into each well. The luminescence of Renilla luciferase was measured with an integration time of 10 seconds. A relative luminescence of the cells when treated with the Vitidis Vinferae Radix extract was calculated based on a luminescence of 100 when treated with DMSO. The hepatotoxicity of the Vitidis Vinferae Radix extract was also analyzed in the same manner as in Experimental Example 1. The results were shown in FIGS. 3 to 7.

As shown in FIGS. 3 to 7, it was determined that the cells treated with the Vitidis Vinferae Radix ethyl acetate fraction, butanol fraction, ethanol extract, hexane fraction, water fraction at a concentration of 0.1 ng/ml to 10 µg/ml exhibited excellent inhibitory activity on HCV genome replication, thus inhibiting proliferation of HCV, and had no hepatotoxicity.

The inhibitory activity on HCV genome replication of the Vitidis Vinferae Radix methanol extract was shown in FIG. 1, and it was determined that the Vitidis Vinferae Radix methanol extract also exhibited inhibitory activity on HCV genome replication and no hepatotoxicity.

Experimental Example 3. Measurement of Inhibitory Activity on Protein Expression of Hepatitis C Virus of Vitidis Vinferae Radix Extract The following experiment was performed in order to determine whether inhibitory activity on genome replication of the hepatitis C virus of the Vitidis Vinferae Radix methanol extract determined in Experimental Example 2 results in inhibitory activity on protein expression of the hepatitis C virus or not.

Figure 8:
FIG. 8 is a view showing a genome structure of a subgenomic replicon Bart79I-NS5A-GFP HCV reporter virus used to measure protein expression of the hepatitis C virus.

First, the amount of fluorescence of a green fluorescent protein (GFP) was measured using a fluorescence-activated cell sorter (FACS) in order to determine the degree of protein expression of the hepatitis C virus when injected with the Vitidis Vinferae Radix methanol extract using Bart79I which is a subgenomic replicon of the hepatitis C virus of genotype 1b shown in FIG. 8. The results were shown in FIG. 9.

Figure 9:
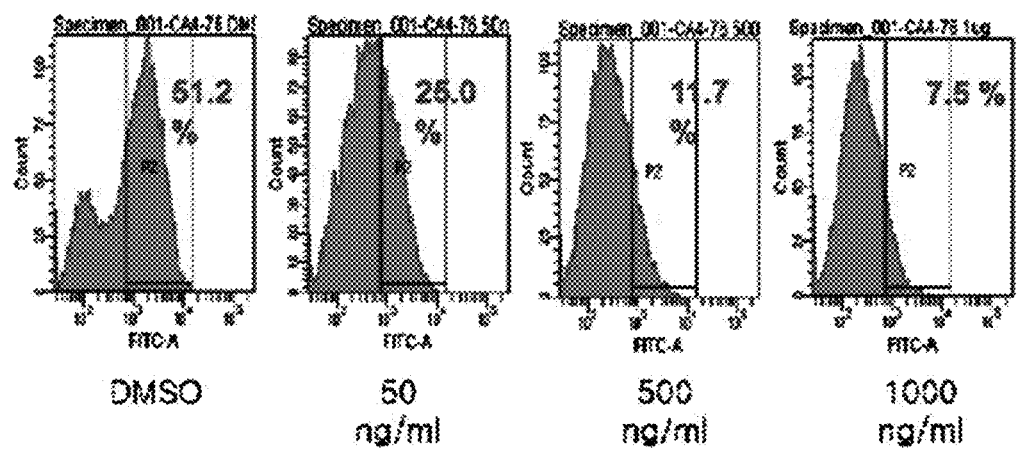
FIG. 9 is a view showing the influence of the Vitidis Vinferae Radix methanol extract according to the present invention on the protein expression of the hepatitis C virus by measuring the amount of green fluorescence expressed in a hepatocyte including a subgenomic replicon Bart79I-NS5A-GFP illustrated in FIG. 8 using fluorescence assorted cell sorter (FACS).

As shown in FIG. 9, it was determined that, when the Vitidis Vinferae Radix methanol extract according to the present invention was injected at a concentration of 50 ng/ml to 1 µg/ml, the amount of fluorescence of GFP expressed in liver cells significantly decreased. Accordingly, the Vitidis Vinferae Radix methanol extract was determined to have inhibitory activity on virus protein expression attributable to inhibition of genome replication of the hepatitis C virus.

Figure 10:
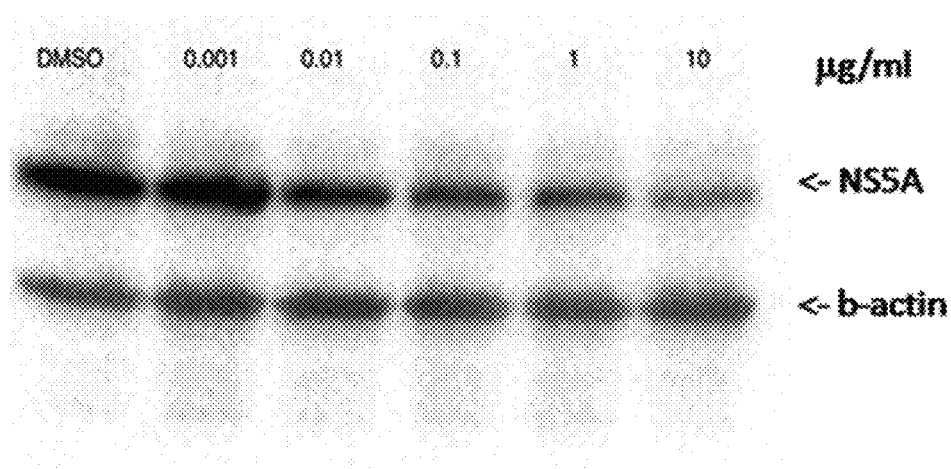
FIG. 10 is a view showing the influence of the Vitidis Vinferae Radix methanol extract according to the present invention on the protein expression of the hepatitis C virus by measuring an amount of a host cell beta actin protein and an amount of proteins of a virus NS5A protein using a Western blot.

Additionally, amounts of proteins of a virus NS5A protein and host cell beta actin proteins were measured to determine the influence of the Vitidis Vinferae Radix methanol extract according to the present invention on the protein expression of the hepatitis C virus by using a Western blot, and the results were shown in FIG. 10.

As shown in FIG. 10, it was determined that, when the Vitidis Vinferae Radix methanol extract according to the present invention was injected at a concentration of 50 ng/ml to 1 µg/ml, the protein expression of the hepatitis C virus in hepatoma cell lines infected with the hepatitis C decreased in a concentration-dependent manner. Accordingly, the Vitidis Vinferae Radix methanol extract was determined to have inhibitory activity on virus protein expression attributable to inhibition of genome replication of the hepatitis C virus.

Formulation examples of the pharmaceutical composition including the extract according to the present invention will be described in detail. However, these formulation examples are for illustrative purposes only and are not intended to limit the scope of the present invention.

Formulation Example 1. Preparation of Pharmaceutical Composition 1-1. Preparation of Powder
Vitidis Vinferae Radix extract or fraction thereof 20 mg
lactose 100 mg
talc 10 mg
The above-described components are mixed and a sealing pack was filled with the mixture to prepare powders.

1-2. Preparation of Tablet
Vitidis Vinferae Radix extract or fraction thereof 10 mg
corn starch 100 mg
lactose 100 mg
magnesium stearate 2 mg
The above-described components are mixed and compressed into tablets according to a conventional tablet preparation method.

1-3. Preparation of Capsule
Vitidis Vinferae Radix extract or fraction thereof 10 mg
crystalline cellulose 3 mg
lactose 14.8 mg
magnesium stearate 0.2 mg
The above-described components are mixed according to a conventional capsule preparation method, and then filled into a gelatin capsule, thereby producing the capsule formulation.

1-4. Preparation of Injection
Vitidis Vinferae Radix extract or fraction thereof 10 mg
mannitol 180 mg
Injectable sterile distilled water 2974 mg
$Na_2HPO_4 \cdot 2H_2O$ 26 mg An injection containing the components having amounts described above per one ampule (2 ml) was prepared according to a conventional injection preparation method.

1-5. Preparation of Liquid
Vitidis Vinferae Radix extract or fraction thereof 20 mg
isomerized glucose syrup 10 g
mannitol 5 g
purified water proper These components were mixed after added with a lemon flavor, and added with purified water so that the volume of the entire solution was 100 ml. These components were filled into a brown bottle, and sterilized to prepare liquids according to a conventional liquid preparation method.

Formulation Example 2. Preparation of Food Composition 2-1. Preparation of Health Functional Food
Vitidis Vinferae Radix extract or fraction thereof 100 mg
vitamin mixture optimum amount
vitamin A acetate 70 μg
vitamin E 1.0 mg
vitamin B1 0.13 mg
vitamin B2 0.15 mg
vitamin B6 0.5 mg
vitamin B12 0.2 μg
vitamin C 10 mg
biotin 10 μg
nicotinic acid amide 1.7 mg
folic acid 50 μg
calcium pantothenate 0.5 mg
mineral mixture optimum amount
ferrous sulfate 1.75 mg
zinc oxide 0.82 mg
magnesium carbonate 25.3 mg
first potassium phosphate 15 mg
second calcium phosphate 55 mg
potassium citrate 90 mg
calcium carbonate 100 mg
magnesium chloride 24.8 mg The above ratio of vitamins and minerals illustrates a preferred example of mixing ingredients relatively suitable for a health functional food, but it can be arbitrarily changed. According to a conventional health functional food preparation method, the above ingredients are mixed and used for preparation of a health functional food composition by a conventional method.

2-2. Preparation of Health Functional Food
Vitidis Vinferae Radix extract or fraction thereof 100 mg
vitamin C 15 g
vitamin E (powder) 100 g
lactic acid iron 19.75 g
zinc oxide 3.5 g
nicotinic acid amide 3.5 g
vitamin A 0.2 g
vitamin B1 0.25 g
vitamin B2 0.3 g
water optimum amount According to a conventional health functional beverage preparation method, the above ingredients were mixed, stirred and heated at 85° C. for about 1 hour, and the prepared solution was filtered, filled into 2 L sterile bottles, sealed, sterilized, and kept under refrigeration, and then used for preparation of a health functional beverage composition according to the present invention.

The above-described composition ratio illustrates a preferred example of mixing ingredients relatively suitable for a beverage, but it can be arbitrarily changed according to regional and national preferences such as local demand, national demand, uses, etc.

The above description about the present invention is merely for exemplifying, and it is to be appreciated that those skilled in the art can easily change or modify the embodiments without departing from the scope and spirit of the present invention. Therefore, it should be understood that the foregoing embodiments are provided only for purposes of illustration and not in any way as limiting the present invention.

INDUSTRIAL APPLICABILITY

The Vitidis Vinferae Radix extract or fraction thereof according to the present invention has remarkably low hepatotoxicity and exhibits an excellent effect of selectively inhibiting genome replication of the hepatitis C virus, and thus can be useful for preventing or treating hepatitis C.

The invention claimed is:
1. A method for treating hepatitis C in a patient with hepatitis C, comprising administering to said patient an effective amount of a composition comprising a fraction of an aqueous and/or $C_1$-$C_4$ alcoholic extract of Vitidis Vinferae Radix as an active ingredient,
wherein the fraction is obtained via sequentially fractionating the aqueous and/or alcoholic extract with:
(a) hexane;
(b) hexane and then ethyl acetate;
(c) hexane, ethyl acetate, and then butanol; or
(d) hexane, ethyl acetate, butanol, and then water.
2. The method of claim 1, wherein the alcoholic extract is a methanol or ethanol extract.
3. The method of claim 1, wherein the fraction of Vitidis Vinferae Radix has a selective inhibitory activity on RNA genome replication of hepatitis C virus.

* * * * *